United States Patent
Tojo

(10) Patent No.: US 11,812,925 B2
(45) Date of Patent: Nov. 14, 2023

(54) MOVEMENT ASSISTANCE SYSTEM AND MOVEMENT ASSISTANCE METHOD FOR CONTROLLING OUTPUT OF POSITION ESTIMATION RESULT

(71) Applicant: OLYMPUS CORPORATION, Tokyo (JP)

(72) Inventor: Ryo Tojo, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 555 days.

(21) Appl. No.: 17/079,610

(22) Filed: Oct. 26, 2020

(65) Prior Publication Data

US 2021/0052136 A1 Feb. 25, 2021

Related U.S. Application Data

(63) Continuation of application No. PCT/JP2018/017097, filed on Apr. 26, 2018.

(51) Int. Cl.
*A61B 1/00* (2006.01)
*G06N 20/00* (2019.01)
*A61B 1/005* (2006.01)

(52) U.S. Cl.
CPC .... *A61B 1/000094* (2022.02); *A61B 1/00045* (2013.01); *A61B 1/0051* (2013.01); *A61B 1/000096* (2022.02); *G06N 20/00* (2019.01)

(58) Field of Classification Search
None
See application file for complete search history.

(56) References Cited

U.S. PATENT DOCUMENTS

| 8,285,016 B2 * | 10/2012 | Tanaka | A61B 1/00147 382/128 |
| 2005/0010082 A1 * | 1/2005 | Nishimura | A61B 1/00147 600/145 |

(Continued)

FOREIGN PATENT DOCUMENTS

| EP | 1437083 A1 | 7/2004 |
| JP | 2003-093328 A | 4/2003 |

(Continued)

OTHER PUBLICATIONS

International Search Report dated Jul. 24, 2018 received in PCT/JP2018/017097.

*Primary Examiner* — John P Leubecker
(74) *Attorney, Agent, or Firm* — Scully, Scott, Murphy & Presser, P.C.

(57) ABSTRACT

An movement assistance system includes a processor. The processor detects a position in picked-up images of an image of an image pickup target, causes a memory to store the position, estimates a change in the position of the image pickup target, estimates the position of the image pickup target and performs control for causing a display apparatus to display an estimation result of the position of the image pickup target, when detecting a disappearance state in which the image of the image pickup target is not detected, and performs control for causing the display apparatus not to display the estimation result of the position of the image pickup target when detecting, after the image pickup target is brought into the disappearance state, that a position indicated by the estimation result of the position of the image pickup target is a position inside an output determination region.

13 Claims, 12 Drawing Sheets

(56) References Cited

U.S. PATENT DOCUMENTS

| | | | | |
|---|---|---|---|---|
| 2007/0242899 A1* | 10/2007 | Satoh | ............... | G06T 7/73 |
| | | | | 382/286 |
| 2008/0004603 A1* | 1/2008 | Larkin | ............... | A61B 34/10 |
| | | | | 606/1 |
| 2011/0254937 A1* | 10/2011 | Yoshino | ............... | A61B 1/0655 |
| | | | | 348/E7.085 |
| 2015/0078615 A1* | 3/2015 | Staples, II | ............... | G06T 7/50 |
| | | | | 382/103 |
| 2016/0345802 A1* | 12/2016 | Nir | ............... | A61B 1/00045 |
| 2016/0360120 A1* | 12/2016 | Inoue | ............... | H04N 23/00 |
| 2018/0098685 A1* | 4/2018 | Osawa | ............... | A61B 1/00147 |
| 2018/0228343 A1* | 8/2018 | Seeber | ............... | A61B 34/35 |
| 2019/0043188 A1* | 2/2019 | Wang | ............... | G06T 7/62 |
| 2020/0037856 A1* | 2/2020 | Watanabe | ............... | A61B 1/00045 |
| 2020/0170485 A1* | 6/2020 | Takahashi | ............... | A61B 1/04 |

FOREIGN PATENT DOCUMENTS

| | | | |
|---|---|---|---|
| JP | 2011-224038 A | 11/2011 | |
| JP | 2012-170641 A | 9/2012 | |
| WO | 2008/155828 A1 | 12/2008 | |
| WO | 2017/006449 A1 | 1/2017 | |

* cited by examiner

MOVEMENT ASSISTANCE SYSTEM AND MOVEMENT ASSISTANCE METHOD FOR CONTROLLING OUTPUT OF POSITION ESTIMATION RESULT

CROSS-REFERENCE TO RELATED APPLICATION

This application is a continuation application of PCT/JP2018/017097 filed on Apr. 26, 2018, the entire contents of which are incorporated herein by this reference.

BACKGROUND OF THE INVENTION

1. Field of the Invention

The present invention relates to a movement assistance system and a movement assistance method that enable easy insertion of an endoscope insertion portion and the like.

2. Description of the Related Art

Conventionally, endoscopes have been widely used, and such endoscopes are configured to perform observation and various treatments on a site to be examined by an elongated insertion portion being inserted into a body cavity and the like. In addition, also in the industrial fields, industrial endoscopes have been widely used. Such industrial endoscopes are capable of observing and inspecting a flaw, corrosion, etc., inside a boiler, a turbine, an engine, a chemical plant, and the like.

Endoscopic images obtained by an image pickup device of an endoscope are transmitted to a processor that performs signal processing. The processor performs signal processing on the images from the endoscope, to supply the signal-processed images to a monitor, as images for display, or supply to a recording device, as images for recording.

An insertion portion of an endoscope is inserted into a lumen and the like, in order to examine and diagnose an examination site. In examination and diagnosis, it is desirable that an insertion portion is smoothly inserted into a lumen and the like. To this end, WO2008/155828 discloses a technique for detecting a position of a dark part as a target in an insertion direction and indicating an operation direction based on a past position detection history of the dark part when a user loses sight of the dark part.

SUMMARY OF THE INVENTION

A movement assistance system according to one aspect of the present invention includes a memory and a processor. The processor is configured to: receive picked-up images acquired by an image pickup apparatus fixed to a mobile body, detect an image of an image pickup target included in each of the picked-up images, and detect a position in each of the picked-up images of the detected image of the image pickup target; cause the memory to store the position in each of the picked-up images of the detected image of the image pickup target; estimate a change in the position of the image pickup target relative to each of the picked-up images, by detecting a change in the received picked-up images; estimate the position of the image pickup target relative to each of the picked-up images based on information on the position stored in the memory and an estimation result of the change in the position of the image pickup target, to output a position estimation result, and perform control for causing a display apparatus to display the position estimation result, when detecting a disappearance state in which the image of the image pickup target is not detected on the picked-up images; and perform control for causing the display apparatus not to display the position estimation result, when detecting, after the image of the image pickup target is brought into the disappearance state, that a position indicated by the position estimation result is a position inside an output determination region as a region for determining whether or not to output the position estimation result.

A movement assistance method according to one aspect of the present invention includes: receiving picked-up images acquired by an image pickup apparatus fixed to a mobile body, detecting an image of an image pickup target included in each of the picked-up images, and detecting a position in each of the picked-up images of the detected image of the image pickup target; causing a memory to store the position in each of the picked-up images of the detected image of the image pickup target; estimating a change in the position of the image pickup target relative to each of the picked-up images, by detecting a change in the picked-up images; estimating the position of the image pickup target relative to each of the picked-up images based on information on the position stored in the memory and an estimation result of the change in the position of the image pickup target, to output a position estimation result, and performing control for causing a display apparatus to display the position estimation result, when detecting a disappearance state in which the image of the image pickup target is not detected on the picked-up images; and performing control for causing the display apparatus not to display the position estimation result, when detecting, after the image of the image pickup target is brought into the disappearance state, that a position indicated by the position estimation result is a position inside an output determination region as a region for determining whether or not to output the position estimation result.

DETAILED DESCRIPTION OF THE PREFERRED EMBODIMENT(S)

Hereinafter embodiments of the present invention are described in detail with reference to drawings.

First Embodiment

Figure 1:
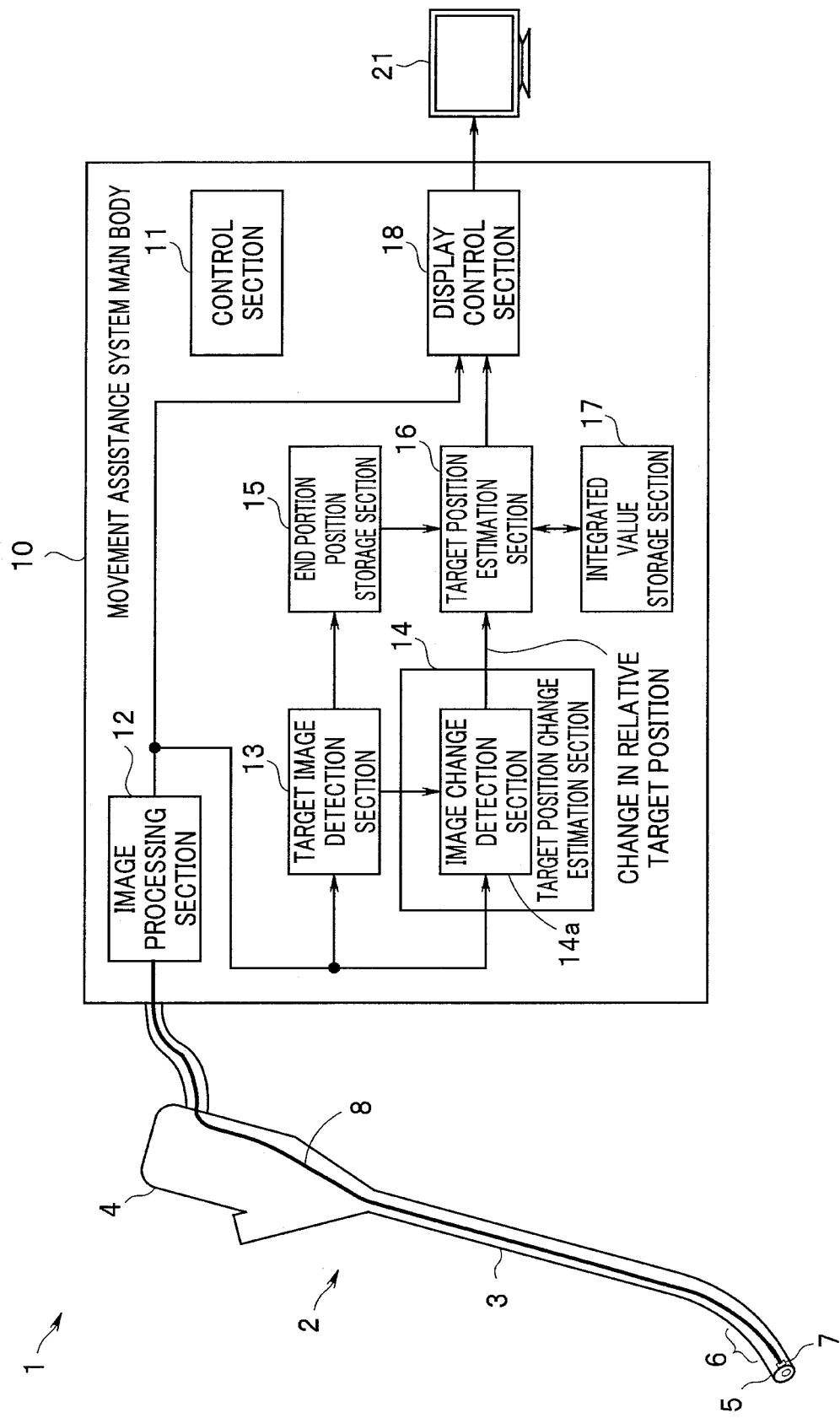
FIG. 1 is a block diagram illustrating a movement assistance system according to a first embodiment of the present invention.

FIG. 1 is a block diagram illustrating a movement assistance system according to the first embodiment of the present invention. The first embodiment is applied to insertion assistance in a case where an insertion portion of an endoscope is inserted into a subject.

The present embodiment is intended to effectively assist a movement of a mobile body which includes an image pickup section and is configured to move, by enabling a presentation or a control of a direction in which the mobile body is to be moved when operation or control for the movement of the mobile body is performed. For example, not only an insertion portion of a medical or industrial endoscope, but also a capsule endoscope, a catheter provided with an image pickup section, and the like are adoptable as the mobile body. Furthermore, various kinds of known autonomously movable devices can be adopted as the mobile body. For example, a robot cleaner movable in a room, an automatic traveling vehicle that moves on the ground, an unmanned aerial vehicle such as a drone can be adopted, or an autonomous ship that moves on the water and the like may be adopted.

In FIG. 1, a movement assistance system 1 includes an endoscope 2, a movement assistance system main body 10, and a display apparatus 21. The endoscope 2 includes an elongated insertion portion 3 and an operation portion 4 which is configured to be operated by an operator and provided so as to be continuous with the proximal end portion of the insertion portion 3. The insertion portion 3 includes, at the distal end thereof, a distal end rigid portion 5, and includes, at the rear end of the distal end rigid portion 5, a bending portion 6 which is configured by a plurality of bending pieces. The bending portion 6 can be bent by operating a bending operation knob, not illustrated, disposed at the operation portion 4.

An image pickup section 7 including an image pickup device configured by CCD, CMOS sensor, and the like is disposed in the distal end rigid portion 5 of the insertion portion 3. The insertion portion 3 is provided with a light guide, not illustrated, for guiding illumination light. The illumination light from a light source, not illustrated, is guided by the light guide and applied from the distal end rigid portion 5 of the insertion portion 3 to a photographing object.

Return light from the photographing object is incident from the distal end rigid portion 5 of the insertion portion 3 to be image-formed on an image pickup surface of the image pickup section 7. The image pickup section 7 acquires an image pickup signal based on an optical image of the photographing object by performing photoelectric conversion. The image pickup section 7 is configured to transmit the image pickup signal to the movement assistance system main body 10 through a signal line 8 in the insertion portion 3 and the operation portion 4.

When an object to be observed by the endoscope 2 is an intestinal tract or the like of a human body, for example, a direction in which the distal end rigid portion 5 is to be moved (hereinafter, referred to as a moving target direction) at the time of examination or the like is a direction of a lumen which is formed by a tubular organ such as an intestinal tract. The image pickup direction of the image pickup section 7 is set in the same direction as the axis direction of the distal end rigid portion 5, for example. Therefore, if an image of an object (hereinafter, referred to as an image pickup target) existing in the moving target direction (hereinafter, referred to as an image pickup target image), that is, an image of a lumen is included in a picked-up image obtained by the image pickup section 7, it can be considered that the distal end rigid portion 5 moves toward the moving target direction.

In other words, at the time of insertion of the insertion portion 3, if an operator performs insertion operation such that the image part of the lumen is included in the picked-up image, it means that the insertion portion 3 is surely advancing in a deep part direction of the lumen. However, when the image of the lumen has temporarily disappeared from the picked-up image, it is not easy to recognize the direction of the lumen based on the picked-up image, because the insertion portion 3 rotates around the axis. In view of the above, the present embodiment applies the picked-up image to the movement assistance system main body 10, to thereby enable the moving target direction to be presented by the moving assistance system main body 10.

The movement assistance system main body 10 is provided with a control section 11. The control section 11 may be configured by a processor using a CPU and the like, and may operate according to a program stored in a memory, not illustrated, to control respective sections, or may implement a part of or all of the functions of the respective sections by an electronic circuit of hardware. The control section 11 controls the respective sections of the movement assistance system main body 10.

An image processing section 12 of the movement assistance system main body 10 is configured to perform predetermined signal processing on an image pickup signal transmitted through the signal line 8 to acquire a picked-up image based on the image pickup signal. The image processing section 12 is configured to output the picked-up image acquired by the image pickup section 7 to a target image detection section 13 and a target position change estimation section 14.

The target image detection section 13 detects an image pickup target image in the picked-up image. For example, the target image detection section 13 may detect the image pickup target image in the picked-up image by using deep learning, for example, R-CNN (Regions with CNN (Convolution Neural Network) features) using CNN, FCN (Fully Convolutional Networks), or the like, for the image pickup target image.

In addition, in the case where the image pickup target is a lumen, the target image detection section 13 may detect the image pickup target image based on a dark part in the picked-up image. When a consecutive region having a predetermined size and a luminance value equal to or less than a predetermined value exists, for example, the target image detection section 13 may determine that the region is the image of the lumen. Furthermore, when the shape of the image pickup target image is a known shape, the target image detection section 13 may detect the image pickup target image based on a feature value of the image pickup target image to track the detected image pickup target image.

In the present embodiment, the target image detection section 13 detects the image pickup target image in the picked-up image and obtains a position on the picked-up image of the detected image pickup target image. In the case where the image pickup target deviates from the image pickup range to be positioned outside the image pickup range, that is, the detected image pickup target image does not exist in (has disappeared from) the picked-up image, the target image detection section 13 outputs, to an end portion position storage section 15, information on the last position on the picked-up image at which the image pickup target image has existed in the picked-up image, that is, information on the position of the image pickup target image at the time of the start of disappearance. In addition, at the time of the start of disappearance of the image pickup target image, the target image detection section 13 outputs disappearance start information to the target position change estimation section 14. The end portion position storage section 15 is configured by a predetermined storage medium, and stores information from the target image detection section 13.

Note that, when detecting the image pickup target image in the picked-up image, the target image detection section 13 may output, for each detection, the information on the position on the picked-up image of the image pickup target image to the end portion position storage section 15. Also in this case, the information on the last position on the picked-up image of the image pickup target image, the position having been detected lastly immediately before the disappearance of the image pickup target image, is stored in the end portion position storage section 15.

The target position change estimation section 14 is configured to receive picked-up images from the image processing section 12, to detect, based on a change in the picked-up images, a change in the relative position of the image pickup target (hereinafter, referred to as a target position) with respect to the distal end rigid portion 5 from the time point of the start of disappearance of the image pickup target image. Since the image pickup section 7 is fixed to the distal end rigid portion 5, it can be said that the relative position of the image pickup target with respect to the distal end rigid portion 5 is a target position of the image pickup target, with the image pickup range of the image pickup section 7 as a reference, i.e., the target position of the image pickup target relative to each of the picked-up images.

When the operator performs operation of inserting or extracting the insertion portion 3 into or from the lumen such as the intestinal tract of the subject, twisting the insertion portion 3 around the axis of the insertion portion 3, or bending the bending portion 6, for example, the distal end rigid portion 5 moves in a direction orthogonal to the axis direction of the insertion portion 3, in an advancing/retracting direction along the axis direction, and in a rotation direction around the axis of the insertion portion 3. The image pickup section 7 is disposed so as to be fixed to the distal end rigid portion 5, and the image pickup direction (image pickup range) of the image pickup section 7 changes in accordance with the movement of the distal end rigid portion 5. Therefore, observing the change in the image pickup range, i.e., the change in the picked-up images enables the moving amount and the moving direction of the distal end rigid portion 5, that is, the change in the target position to be obtained.

In addition, when the object to be observed by the endoscope 2 is an intestinal tract and the like of a human body, there is a case where the shape of the organ as the site to be observed changes. In such a case, even if the distal end rigid portion 5 is stopped, a position of the lumen with respect to the position of the distal end rigid portion 5 sometimes changes relatively due to displacement of the site to be observed.

In both of the case where the distal end rigid portion 5 moves and the case where the site to be observed is displaced, the relative change between the position of the distal end rigid portion 5 and the position of the image pickup target such as a lumen can be detected based on the change in the picked-up images. The target position change estimation section 14 includes an image change detection section 14a. The image change detection section 14a is configured to detect a change in the image in the picked-up images which are inputted sequentially. The target position change estimation section 14 estimates the change in the relative position of the image pickup target with the distal end rigid portion 5 as a reference, that is, the change in the target position, based on the change in the picked-up images detected by the image change detection section 14a. The target position change estimation section 14 can adopt, for example, an optical flow estimation based on the known image processing or deep learning, as a method for estimating the change in the target position based on the change in the picked-up images.

Figure 2:
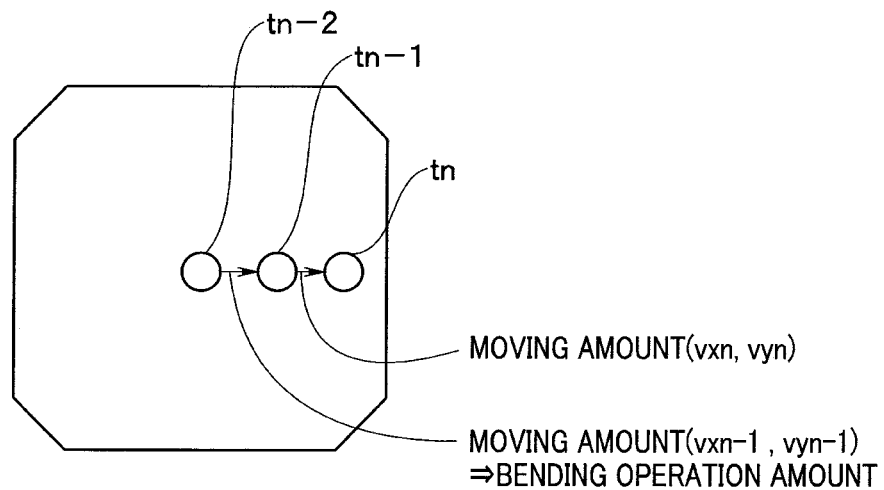
FIG. 2 is an explanatory diagram for explaining an estimation method of a target position by an optical flow.
Figure 3:
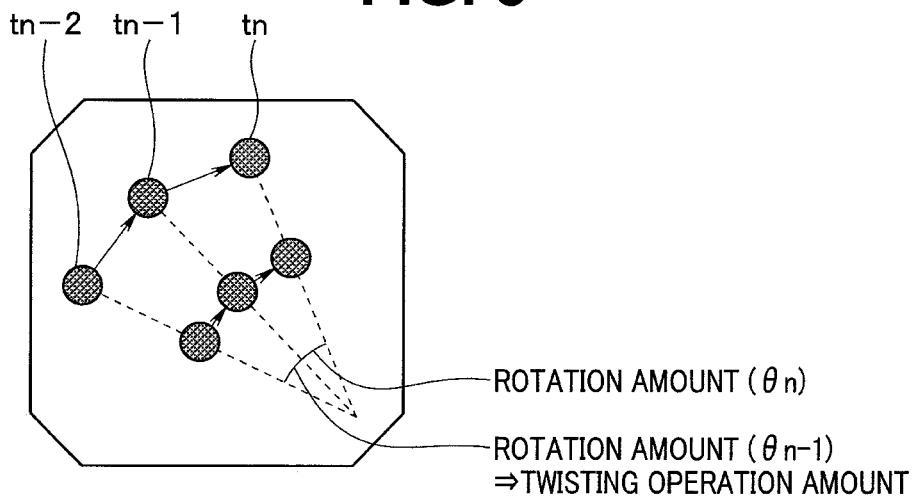
FIG. 3 is an explanatory diagram for explaining the estimation method of the target position by the optical flow.
Figure 4:
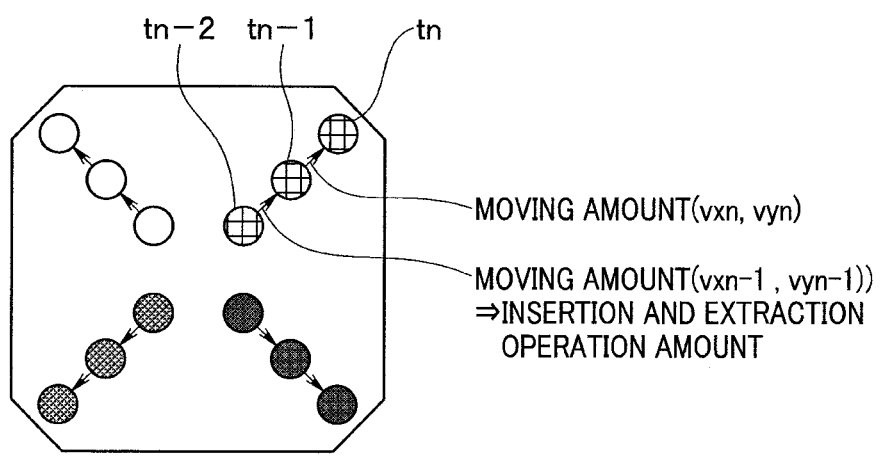
FIG. 4 is an explanatory diagram for explaining the estimation method of the target position by the optical flow.

FIGS. 2 to 4 are explanatory diagrams for explaining the estimation method of a change in the target position by the optical flow estimation. FIGS. 2 to 4 illustrate the image part (hereinafter, also referred to as tracking point or tracking points) of the object included in the picked-up images with the circles. The arrows between the circles indicate the movement of the object. That is, the length of each of the arrows corresponds to the moving amount of the object, and the direction of each of the arrows corresponds to the moving direction of the object. Note that the image of the object may be one pixel, or a predetermined region composed of a plurality of pixels. In FIGS. 2 to 4, the circles of the same pattern indicate the same one object.

FIGS. 2 to 4 each illustrate an example for analyzing the movement of the object from the position of the object at each of the time tn−2, tn−1, and to by an optical flow estimation. FIG. 2 illustrates an example in which a predetermined object linearly moves in the picked-up images, and FIG. 3 illustrates an example in which the predetermined objects move while rotating with a predetermined position as a center in the picked-up images. FIG. 4 illustrates an example in which a plurality of objects respectively move on the linear lines extending radially from a predetermined point in the picked-up images.

The predetermined object in FIG. 2 moves linearly in the picked-up images. FIG. 2 illustrates the change in the position of the object, which is obtained when the operator bends the bending portion 6 in one direction, for example. The predetermined objects in FIG. 3 move so as to form circular arcs in the picked-up images. FIG. 3 illustrates, for example, the change in the position of the object, which is obtained when the operator rotates the insertion portion 3 by twisting the insertion portion in one direction. The respective objects in FIG. 4 move linearly and radially from one point in the picked-up images. FIG. 4 illustrates the change in the position of the objects, which is obtained when the operator inserts the distal end rigid portion 5 into the lumen, for example.

In order to detect the change in the target position illustrated in FIG. 2, the target position change estimation section 14 has only to set one or more tracking points in the picked-up images to obtain the optical flow. Further, in order to detect the change in the target position illustrated in FIG. 3, the target position change estimation section 14 has only to set two or more tracking points in the picked-up images to obtain the optical flow. Furthermore, in order to detect the change in the target positions illustrated in FIG. 4, the target position change estimation section 14 has only to set three or more tracking points in the picked-up images to obtain the optical flow. Note that a characteristic part such as an edge part in the picked-up images may be adopted as the tracking point, or movement of the object may be detected by setting all the pixels in each of the picked-up images as the tracking points, for example.

The target position change estimation section 14 estimates the change in the target position by the optical flow estimation, based on the obtained change in the position of the tracking point from the time of the start of disappearance of the image pickup target image, and outputs the estimation result to a target position estimation section 16. As illustrated in FIG. 2, for example, if it is supposed that the tracking point moves on the screen by the moving amount corresponding to (vxn, vyn) during the time period from the time tn−1 to the time tn, the target position change estimation section 14 estimates that the target position moves by the moving amount (vxn, vyn) in the same direction as the moving direction of the tracking point in FIG. 2 during the time period from the time tn−1 to the time tn.

Furthermore, as illustrated in FIG. 3, for example, if it is supposed that the tracking points move on the screen by a rotation amount θ during the time period from the time tn−1 to the time tn, the target position change estimation section 14 estimates that the target position rotates by the rotation amount θ in the same direction as the moving direction of the tracking points in FIG. 3 during the time period from the time tn−1 to the time tn. Similarly, as illustrated in FIG. 4, for example, if it is supposed that the tracking points move on the screen by the moving amount (vxn, vyn) during the time period from the time tn−1 to the time tn, the target position change estimation section 14 estimates that the target position moves in the insertion direction by the moving amount corresponding to the moving amount (vxn, vyn) in FIG. 4 during the time period from the time tn−1 to the time tn. Note that the moving amount of each of the tracking points and the moving amount of the target position can be considered to be substantially proportional to each other. However, even in a case where there is no proportional relation between the moving amounts, if the rough position or direction of the image pickup target can be known, the distal end rigid portion 5 can be moved to the target position. Therefore, even in the case, the object of the present embodiment can be achieved.

When the object to be observed is the intestinal tract and the like of a human body, a plurality of tracking points in the picked-up images sometimes move irregularly in a manner different from the moving manners illustrated in FIGS. 2 to 4, due to the change in the shape of the organ as the site to be observed. In addition, there is a case where the plurality of tracking points may move irregularly due to erroneous detection of the optical flow by the target position change estimation section 14.

Figure 5:
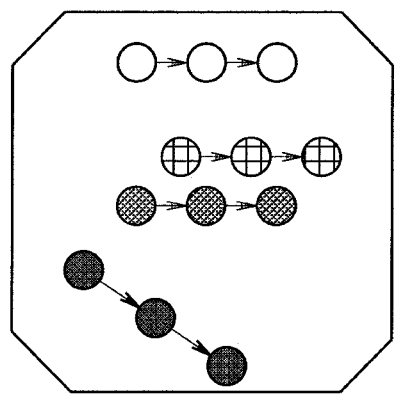
FIG. 5 is an explanatory diagram illustrating an example in which movements of tracking points are irregular.

FIG. 5 is an explanatory diagram illustrating an example in which the movements of the tracking points are irregular. FIG. 5 illustrates the example by the same method as that used in FIGS. 2 to 4. In FIG. 5, the circles of the same pattern indicate the same one object (tracking point). When the plurality of tracking points thus move irregularly, the target position change estimation section 14 may adopt the following methods. For example, the target position change estimation section 14 may find the largest number of tracking points the movements of which are determined to be the same, and use the movement of the tracking points for the estimation of the change in the target position. Alternatively, the target position change estimation section 14 may use the average of the movements of the respective tracking points for the estimation of the change in the target position, for example. Alternatively, for example, in the case of using the average of the movements of the respective tracking points for the estimation of the change in the target position, the target position change estimation section 14 may estimate the change in the target position based on the weighted average obtained by applying weighting according to the number of movements which are determined to be the same movement.

Figure 6:
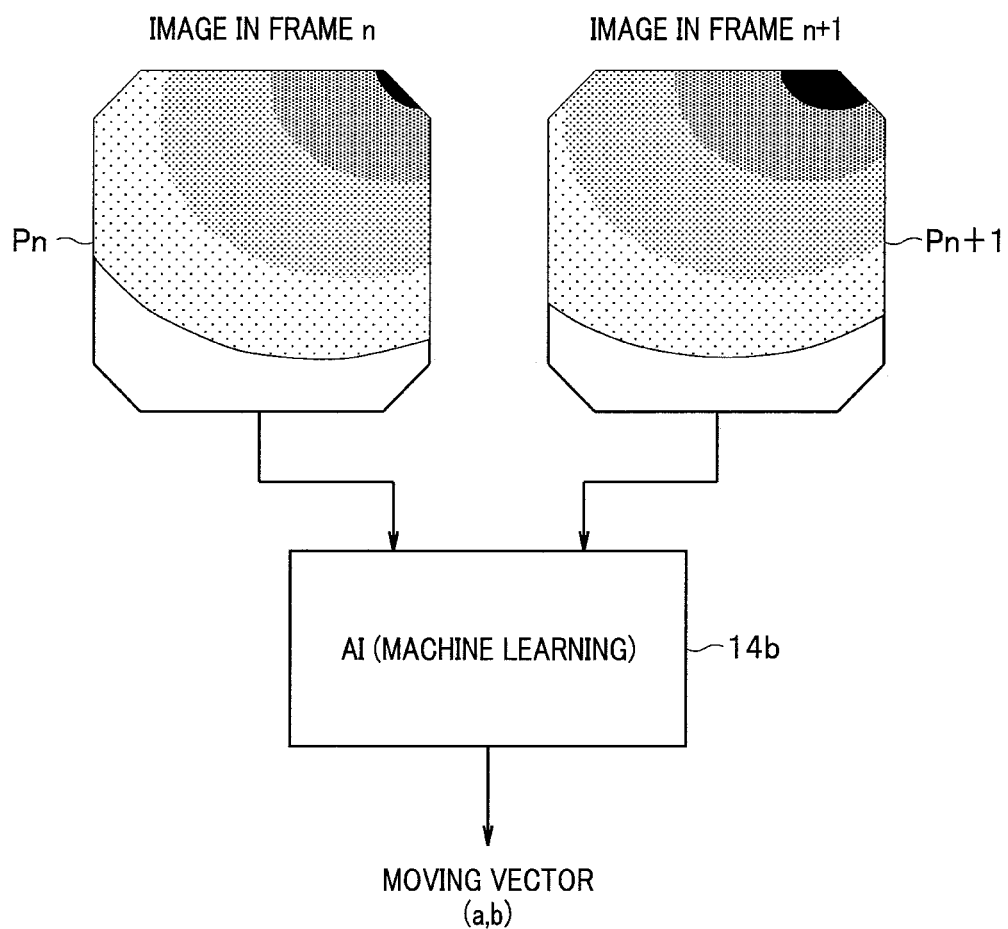
FIG. 6 is an explanatory diagram for explaining the estimation method of the target position by machine learning or deep learning.

FIG. 6 is an explanatory diagram for explaining the estimation method of the change in the target position by machine learning or deep learning. The target position change estimation section 14 may configure an AI (artificial intelligence) 14b that achieves machine learning, deep leaning, or the like. The AI 14b receives, as teacher data, the picked-up images before and after the relative position change of the distal end rigid portion 5 with respect to the image pickup target, to generate a model for estimating the change in the target position corresponding to the change in the picked-up images. The AI 14b uses the generated model to estimate the change in the target position (moving vector (a, b)) in the case where a picked-up image Pn in a frame n has changed to a picked-up image Pn+1 in a frame n+1. The target position change estimation section 14 outputs information on the change in the target position estimated by the AI 14b to the target position estimation section 16.

The target position estimation section 16 reads, from the end portion position storage section 15, the information on the position at the time of the start of disappearance of the image pickup target image. The target position estimation section 16 estimates a current position of the image pickup target (target position) relative to the picked-up image, based on the position of the image pickup target image at the time of the start of disappearance of the image pickup target image and the change in the target position estimated by the target position change estimation section 14. Here, the change in the target position corresponds to a change amount, with the time of the start of disappearance of the image pickup target image as a reference. In the case where the time of the start of disappearance of the image pickup target image is time to, if it is supposed that the change amount by the time to is Δx, Δy, the change amount Δx, Δy is obtained by the following equation (1). The target position estimation section 16 provides the estimation result of the target position to an integrated value storage section 17 to cause the integrated value storage section 17 to store the estimation result. Furthermore, the target position estimation section 16 reads out, from the integrated value storage section 17, the estimation result to sequentially update the estimation result of the target position by using the information on the change in the target position obtained from the target position change estimation section 14. If it is supposed that the estimated position of the image pickup target is x, y, and the position of the image pickup target image at the time of the start of disappearance is $x_0$, $y_0$, the estimated position x, y is obtained by the following equation (2). The integrated value storage section 17 is configured by a predetermined recording medium, and stores the information from the target position estimation section 16.

$$\Delta x = \sum_{i=0}^{n} v_{xi} \quad (1)$$

$$\Delta y = \sum_{i=0}^{n} v_{yi}$$

$$x = x_0 + \Delta x \quad (2)$$

$$y = y_0 + \Delta y$$

The target position estimation section 16 outputs the estimation result of the target position also to a display control section 18. The display control section 18 also receives the picked-up images obtained by the endoscope 2 from the image processing section 12. The display control section 18 generates display data for displaying each of the picked-up images and a sign indicating the moving target direction relative to each of the picked-up images, to output the generated display data to a display apparatus 21. Note that the display control section 18 may display the sign indicating the current position of the image pickup target (target position) relative to each of the picked-up images, together with the sign indicating the moving target direction, or instead of the sign indicating the moving target direction.

Figure 7:
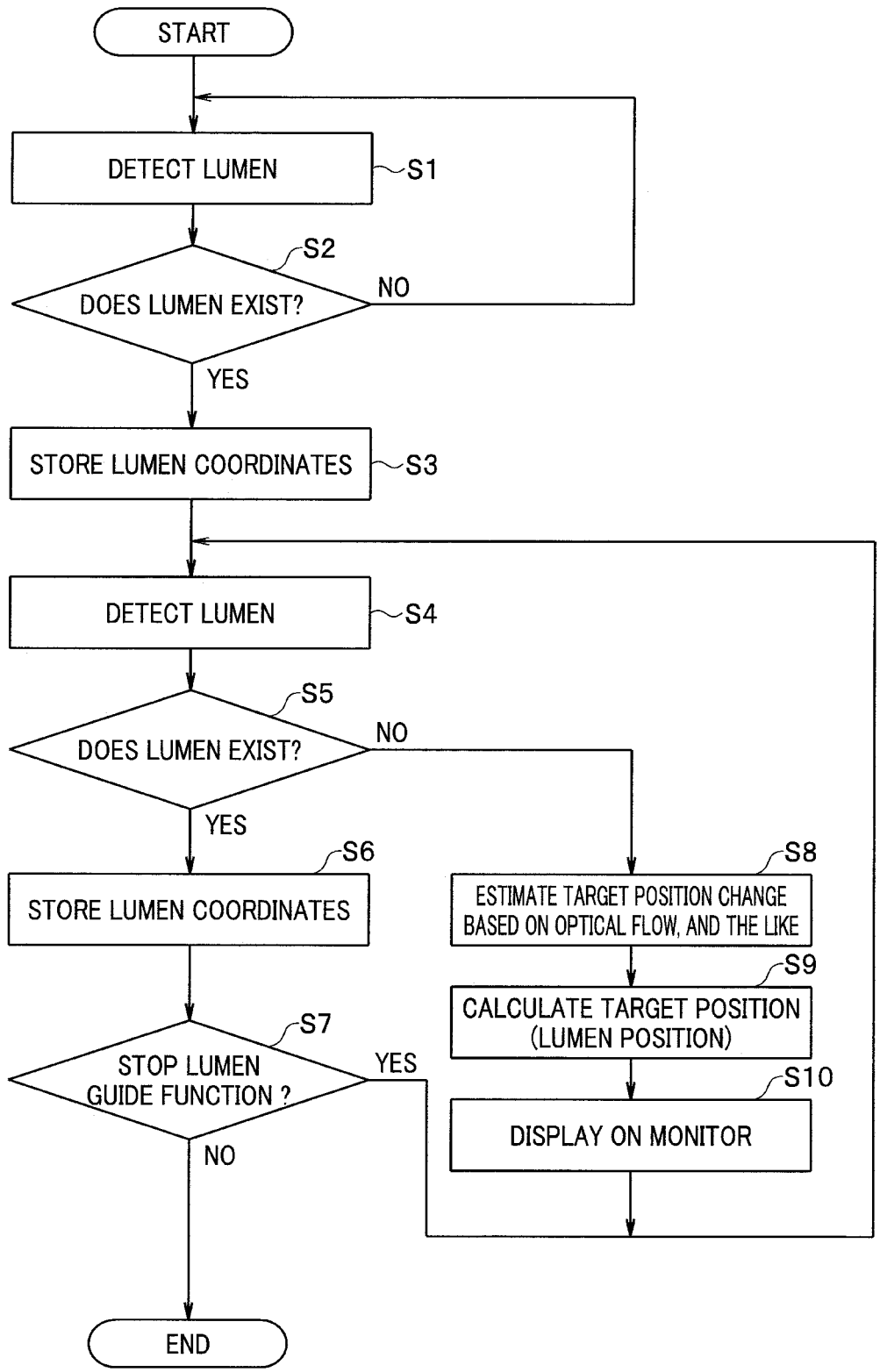
FIG. 7 is a flowchart for explaining an operation according to the first embodiment.

Next, the operation of the embodiment thus configured will be described with reference to FIGS. 7 to 12. FIG. 7 is a flowchart for explaining an operation according to the first embodiment. FIGS. 8 to 12 are explanatory diagrams each explaining the operation according to the first embodiment.

Now, description is made on an example in which the movement assistance system according to the present embodiment is used for an insertion assistance in the case where the insertion portion 3 of the endoscope 2 is inserted into the intestinal tract of the human body.

It is supposed that the operator inserts the insertion portion 3 from the anus of the subject who is lying on an examination bed into the colon of the subject. Images of the condition inside the intestinal tract at the time of the insertion are picked up by the image pickup section 7 provided in the distal end rigid portion 5 of the insertion portion 3. Image pickup signals from the image pickup section 7 are supplied to the image processing section 12 in the movement assistance system main body 10 through the signal line 8. The image processing section 12 performs predetermined signal processing on the image pickup signals to obtain picked-up images. The picked-up images are supplied to the display control section 18 where the picked-up images are converted into a format displayable on the display apparatus 21, and then supplied to the display apparatus 21. Thus, endoscopic images (observation images) at the time of the insertion are displayed on a display screen 21a of the display apparatus 21.

Figure 8:
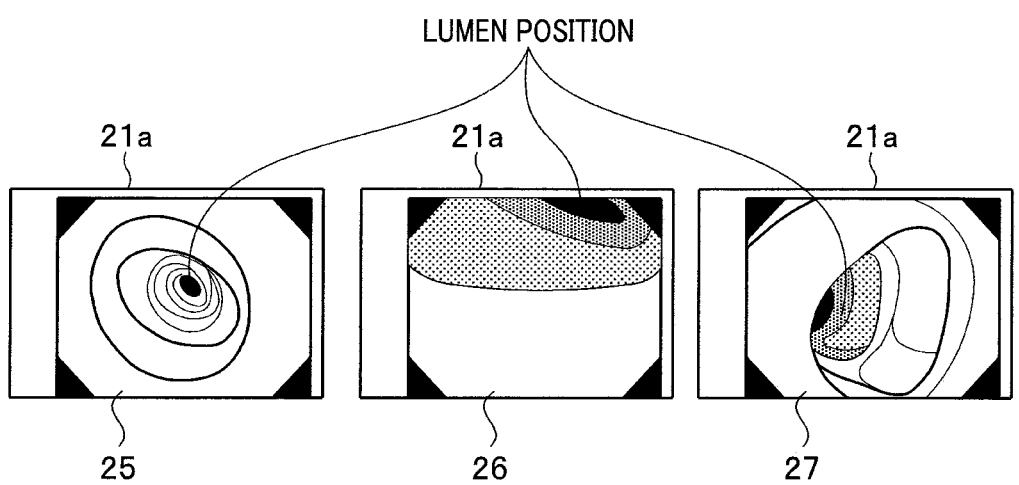
FIG. 8 is an explanatory diagram for explaining the operation according to the first embodiment.

FIG. 8 illustrates examples of the picked-up images (endoscopic images) displayed on the display screen 21a of the display apparatus 21 in this case. The picked-up image 25 in FIG. 8 illustrates that the image part of the lumen having a relatively low luminance is picked up and displayed at the center of the image 25. The axis direction of the distal end rigid portion 5 is directed substantially in the deep part direction of the lumen. Further, the picked-up image 26 in FIG. 8 illustrates that the image part of the lumen having the relatively low luminance is picked up and displayed at the upper part of the image 26. Furthermore, the picked-up image 27 in FIG. 8 illustrates that the image part of the lumen having the relatively low luminance is picked up and displayed at the center of the image 27. The image 27 illustrates that the deep part direction of the lumen exists from the axis direction of the distal end rigid portion 5 toward the left side, with the picked-up image in which the lumen is displayed on the display screen 21a as a reference.

In the states illustrated in the images 26, 27, and the like, if the insertion portion 3 is simply inserted, with the distal end rigid portion 5 directed in the current axis direction, the disappearance state may occur in which the lumen part deviates from the image pickup range and the image part of the lumen is not displayed. The present embodiment provides, in such a disappearance state, a lumen guide function for giving an assistance for guiding the distal end rigid portion 5 in a direction in which the distal end portion 5 is to be moved.

Figure 9:
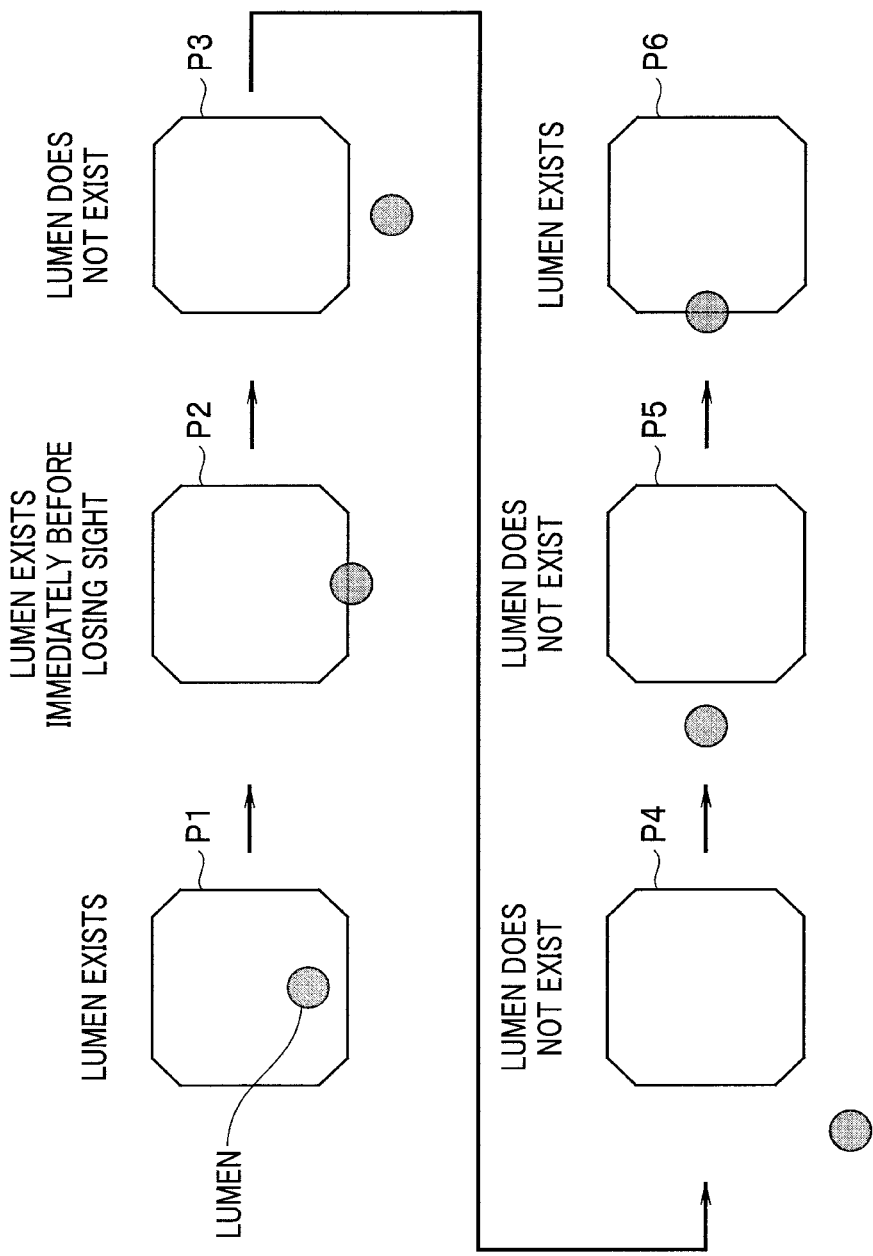
FIG. 9 is an explanatory diagram for explaining the operation according to the first embodiment.

FIG. 9 illustrates the change in the position of the image part of the lumen in the picked-up images, that is, the change in the position on the images of the image pickup target image, in accordance with the movement of the distal end rigid portion 5. FIG. 9 illustrates the image part of the lumen in a simplified manner with the circles. FIG. 9 illustrates that the position of the image part of the lumen (image pickup target image) changes in the picked-up images P1, P2, . . . P6, which are sequentially photographed and obtained, with the elapse of the time indicated by the arrows.

That is, in the example in FIG. 9, the image pickup target image, which is displayed on the lower side of the center of the picked-up image P1 (lumen exists), moves to the lower end of the image in the picked-up image P2 (lumen exists, immediately before losing sight), and deviates from the image range and disappears in the picked-up image P3 (lumen does not exist). Furthermore, in accordance with the movement of the distal end rigid portion 5 and the displacement of the intestinal tract, the image pickup target image moves to the lower left side relative to the picked-up image P4 at the time point of the image pickup of the picked-up image P4 (lumen does not exist), and moves to left relative to the picked-up image P5 at the time point of the image pickup of the picked-up image P5 (lumen does not exist). Then, the image pickup target image is displayed at the left end of the picked-up image P6 at the time point of the image pickup of the picked-up image P6 (lumen exists).

Such disappearance of the image pickup target image is detected by the target image detection section 13. The target image detection section 13 receives a picked-up image from the image processing section 12, and detects the lumen as the image pickup target image in step S1. Next, in step S2, the target image detection section 13 determines whether or not the image pickup target image exists in the picked-up image. The target image detection section 13 repeats the steps S1 and S2 until detecting the image pickup target image. When detecting the image pickup target image, the target image detection section 13 proceeds the processing to step S3, to cause the end portion position storage section 15 to store the position (lumen coordinates) on the image of the detected image pickup target image. For example, the position of the lumen on the picked-up image P1 in FIG. 9 is stored in the end portion position storage section 15.

The target image detection section 13 continues detection of the image pickup target image in step S4, and determines whether or not the image pickup target image exists in the image in step S5. When detecting the image pickup target image, the target image detection section 13 proceeds the processing to step S6, to cause the end portion position storage section 15 to store the position (lumen coordinates) on the image of the detected image pickup target image. For example, the position of the lumen on the picked-up image P2 in FIG. 9 is stored in the end portion position storage section 15.

The control section 11 determines, in next step S7, whether or not an instruction for stopping the lumen guide function is given. When the instruction for stopping the lumen guide function is not given, the control section 11 returns the processing to the step S4, to cause the target image detection section 13 to continue the detection of the lumen. When the instruction for stopping the lumen guide function is given, the control section 11 terminates the processing.

It is supposed that the picked-up image P3 is inputted into the target image detection section 13 after the picked-up image P2 in FIG. 9. The target image detection section 13 proceeds the processing from the step S5 to step S8, to output the disappearance start information indicating that the image pickup target image has disappeared to the target position change estimation section 14. Note that the position coordinates at the center of the lower end of the picked-up image P2 are stored in the end portion position storage section 15. The target position change estimation section 14 receives the picked-up images from the image processing section 12. In the step S8, the target position change estimation section 14 detects the change in the position of the image pickup target image with respect to the distal end rigid portion 5 based on the change in the image in the sequentially received picked-up images, and outputs the information on the change in the relative target position to the target position estimation section 16.

The target position estimation section 16 acquires, from the end portion position storage section 15, the information on the position of the image pickup target image at the time of the start of disappearance, calculates the current position of the image pickup target image based on the information on the change in the relative target position inputted from the target position change estimation section 14, and causes the integrated value storage section 17 to store the obtained current position of the image pickup target image (step S9). The target position estimation section 16 calculates the current position of the image pickup target image, which changes each moment, based on the information on the position stored in the integrated value storage section 17 and the change in the relative target position which is inputted sequentially from the target position change estimation section 14, and updates the current position of the image pickup target image stored in the integrated value storage section 17.

With such a process, the estimation results of the lumen positions at the respective time points of the image pickups of the picked-up images P3, P4, and P5 in FIG. 9 are held while being updated in the integrated value storage section 17.

The target position estimation section 16 outputs the estimated position of the image pickup target image also to the display control section 18. The display control section 18 receives information on the estimated position coordinates of the lumen from the target position estimation section 16, to generate display data of the direction sign indicating the direction of the estimated position of the lumen for the endoscopic image from the image processing section 12. The display control section 18 outputs a synthetic image of the endoscopic image and the direction sign to the display apparatus 21. Thus, on the display screen 21a of the display apparatus 21, the endoscopic image is displayed, and when the image of the lumen does not exist in the endoscopic image, the direction sign indicating the current direction of the lumen is displayed (step S10).

Figure 10:
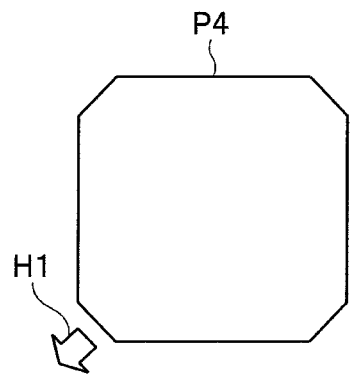
FIG. 10 is an explanatory diagram for explaining the operation according to the first embodiment.

FIG. 10 illustrates a display example of this case. FIG. 10 illustrates a display example at the time point of the image pickup of the picked-up image P4 in FIG. 9. The arrow sign H1 pointing the lower left direction of the picked-up image P4 indicates that the lumen which is the image pickup target at the time of insertion of the insertion portion 3 is positioned at the lower left side with respect to the picked-up image P4.

Figure 11:
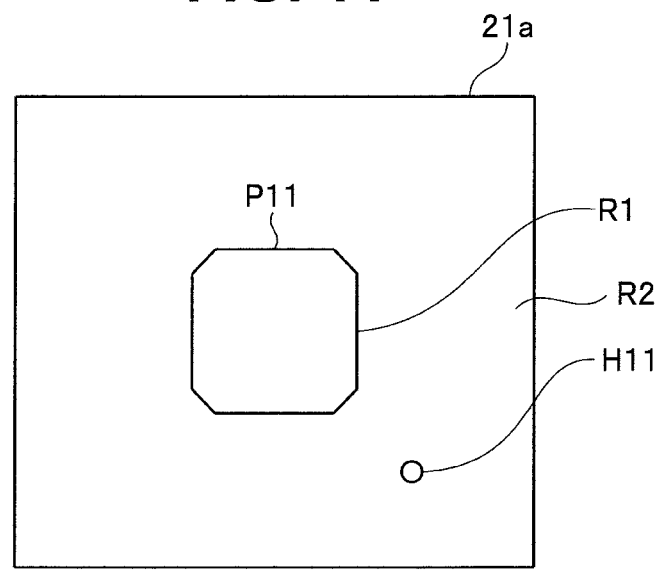
FIG. 11 is an explanatory diagram for explaining the operation according to the first embodiment.
Figure 12:
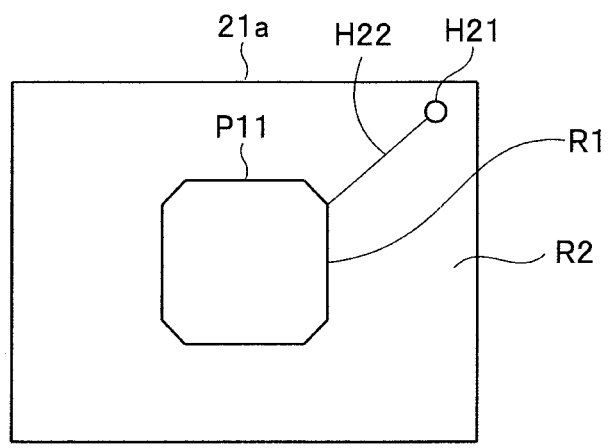
FIG. 12 is an explanatory diagram for explaining the operation according to the first embodiment.

In addition, as described above, the display control section 18 is capable of displaying the sign indicating not only the direction in which the image pickup target exits but also the relative position of the image pickup target with respect to the picked-up image. FIGS. 11 and 12 illustrates display examples of this case.

The example in FIG. 11 illustrates that a display region R1 of a picked-up image P11 is provided at the center of the display screen 21a, and a display region R2 for displaying the relative position of the image pickup target is provided around the display region R1, and a sign H11 indicating the relative position of the image pickup target is displayed in the region R2. In addition, in the example in FIG. 12, not only a sign H21 indicating the relative position of the image pickup target but also a direction sign H22 indicating the direction of the image pickup target with respect to the picked-up image are displayed in the display region R2.

Note that, in the description above, the target position change estimation section 14 detects the change in the relative target position from the time point of the start of disappearance of the image pickup target image. However, the detection of the change in the relative target position may be started before the time of the start of disappearance. In the case where a cumulative estimation error causes a relatively low effects, for example, detection of the change in the relative target position may be started when the image pickup target image enters a predetermined range of the end portion in the picked-up image.

Thus, in the present embodiment, when disappearance of the image pickup target image specifying the direction in which an object is to be moved is detected, the change in the position of the image pickup target image is estimated based on the change in the picked-up images, to thereby estimate the relative position of the image pickup target and enable the sign indicating the estimated relative position or the direction of the image pickup target to be displayed together with each of the picked-up images. With such a configuration, even if the image pickup target image has disappeared from the picked-up images, the operator can easily grasp that the image pickup target is located at which position with respect to each of the picked-up images. As a result, the operator can move the object in the intended direction. Thus, the present embodiment is capable of effectively assisting the movement of the mobile body.

Modification

Figure 13:
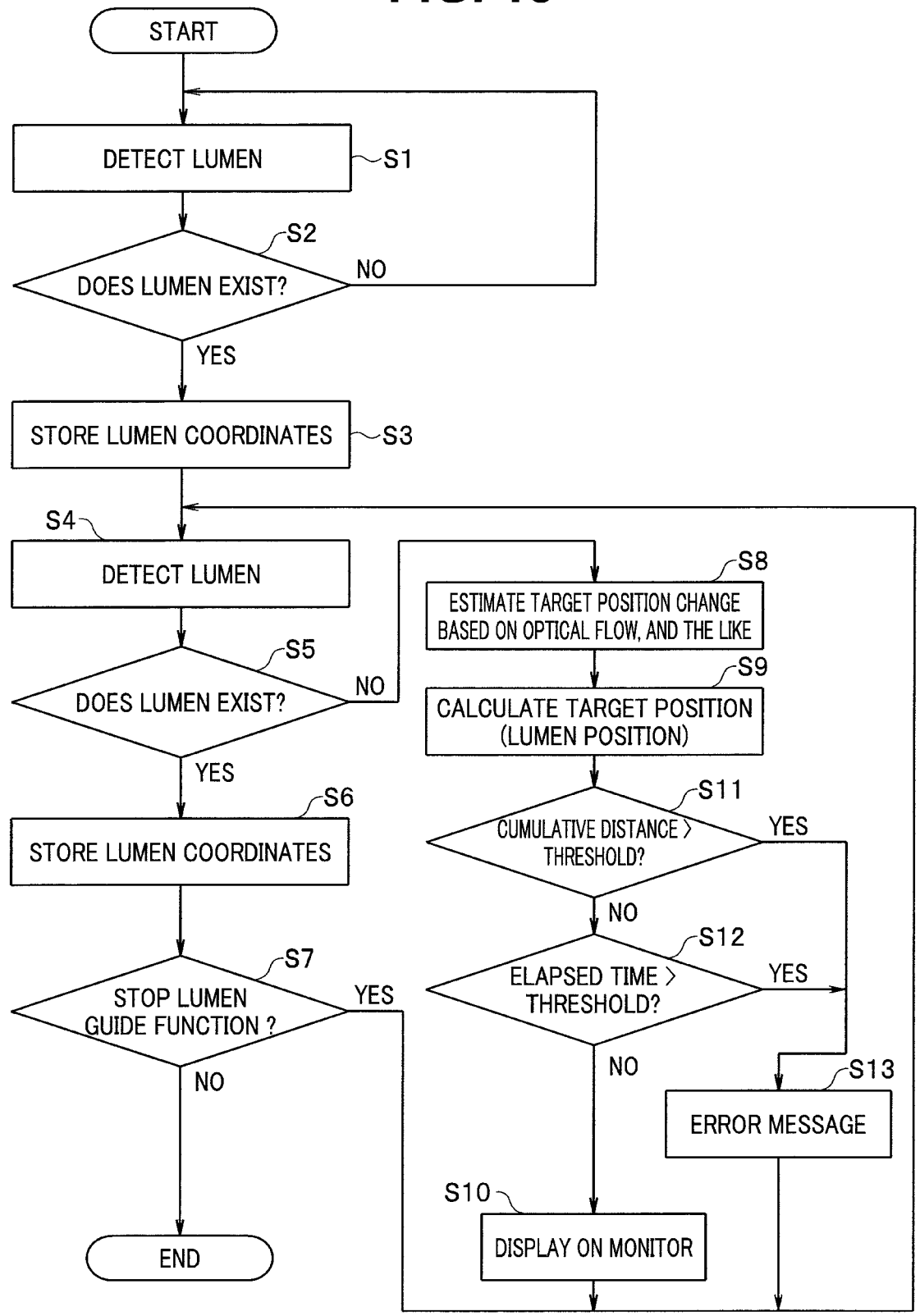
FIG. 13 is a flowchart illustrating a modification.

FIG. 13 is a flowchart illustrating the modification. In the above-described description, the change in the relative target position is detected from the time point of the start of disappearance of the image pickup target image, to thereby estimate the relative position of the image pickup target. However, in the case where the time period from the time point of the start of disappearance is relatively long, or the cumulative value of the change in the target position is large, that is, a direct distance or a route length between the target position relative to the picked-up image at the time point of the start of disappearance and the target position as the estimation result is relatively long, it can be considered that the estimation error of the estimated position of the image pickup target is large. (Hereinafter, description is made on the case where determination is made based on the direct distance, but the same is true on the case where determination is made based on the route length.) Therefore, in the above-described cases, an error message indicating that the estimated direction and position of the image pickup target are not valid may be displayed, or the estimation result may not be displayed.

The control section 11 detects these cases, and causes the display control section 18 to display an error message and the like. The display control section 18 may display the error message such as "estimation of the lumen position is impossible", for example. Alternatively, low reliability of the position sign and the direction sign may be indicated by blinking the direction sign and the position sign.

FIG. 13 is different from the flow in FIG. 7 in that steps S11, S12, and S13 are added. The control section 11 determines, in the step S11, whether or not the integrated value stored in the integrated value storage section 17 exceeds a predetermined threshold. When the integrated value exceeds the predetermined threshold, the control section 11 proceeds the processing to the step S13 to cause the display control section 18 to display the error message or the like.

When determining that the integrated value does not exceed the predetermined threshold in the step S11, the control section 11 determines whether or not the elapsed time from the start of disappearance exceeds a predetermined threshold in the next step S12. When the elapsed time from the start of disappearance exceeds the predetermined threshold, the control section 11 proceeds the processing to the step S13 to cause the display control section 18 to display the error message or the like.

When determining that the elapsed time from the start of disappearance does not exceed the predetermined threshold in the step S12, the control section 11 causes the display control section 18 to perform normal display in the next step S10.

Thus, according to the present modification, when the time period during which the relative position of the image pickup target is estimated is longer than the threshold or the distance to the estimated position is longer than the threshold, the control section 11 regards the reliability of the estimated position as relatively low, to cause the error message to be displayed. This prevents erroneous operation from being performed based on the display with low reliability.

Note that description has been made on the examples in which the thresholds are set for both the cumulative distance and the elapsed time, to display the error message. However, the threshold may be set for either the cumulative distance or the elapsed time.

Second Embodiment

Figure 14:
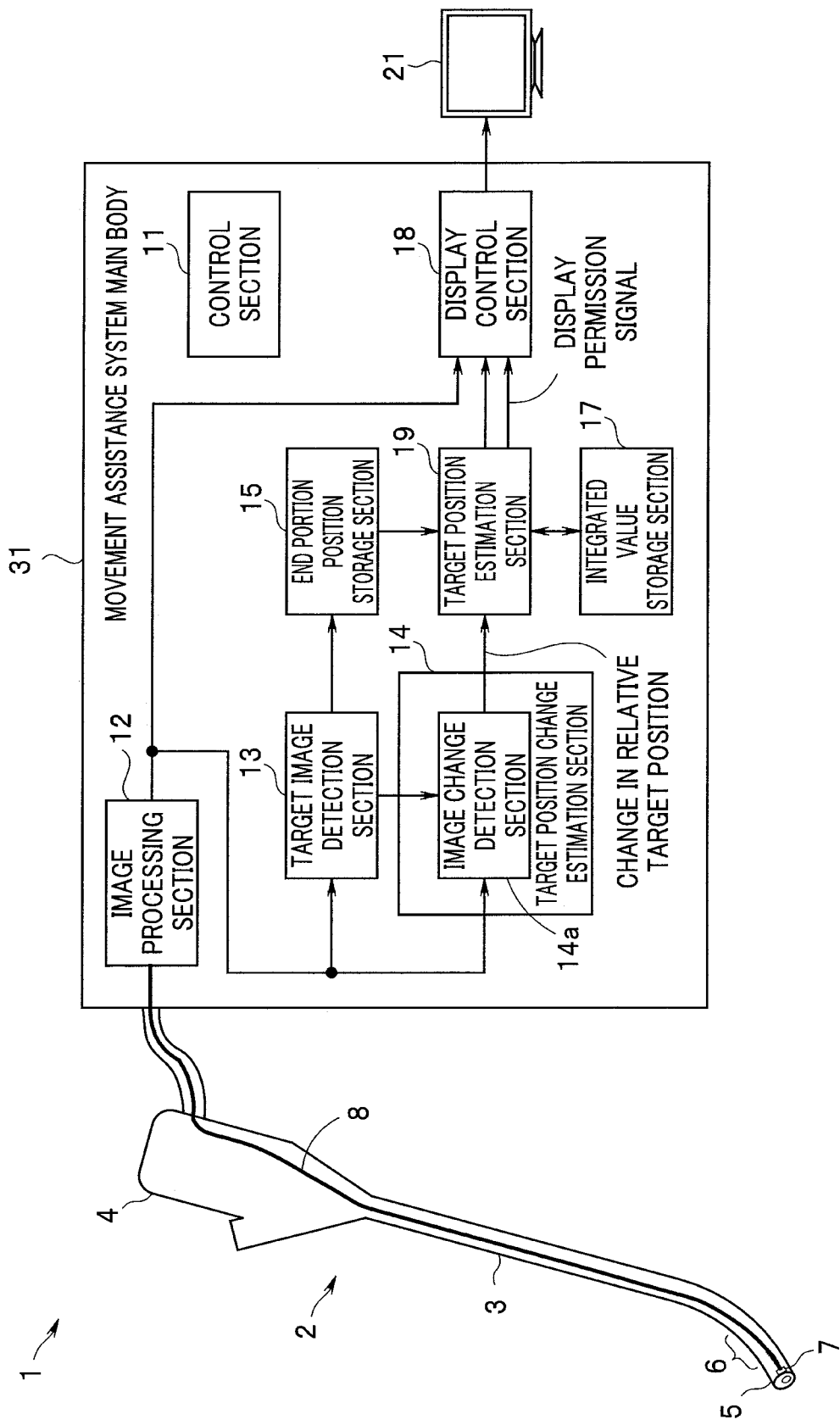
FIG. 14 is a block diagram illustrating a second embodiment of the present invention.

FIG. 14 is a block diagram illustrating the second embodiment of the present invention. The same constituent elements as those in FIG. 1 are attached with the same reference signs in FIG. 14 and descriptions thereof will be omitted.

In the first embodiment, the target position is estimated from the time point when the image pickup target image has been lost from the picked-up image, that is, the time point of the start of disappearance at which disappearance of the image pickup target image is detected. However, there may be a case where the target image detection section 13 cannot detect the image pickup target image even when the image pickup target such as a lumen is located within the image pickup range of the image pickup section 7. The present embodiment copes with such a case.

The present embodiment is different from FIG. 1 in that a movement assistance system main body 31 including a target position estimation section 19 in place of the target position estimation section 16 is employed. A target image detection section 13 detects an image pickup target image in a picked-up image and supplies information on the position in the picked-up image of the detected image pickup target image to an end portion position storage section 15. The end portion position storage section 15 stores the position of the image pickup target image. Furthermore, the end portion position storage section 15 also stores information on a region for determining whether the information on the position at the time of disappearance is valid or invalid (hereinafter, referred to as a target disappearance position determination region) and information on a region for determining whether or not to output the estimated target position (hereinafter, referred to as an output determination region).

Figure 15:
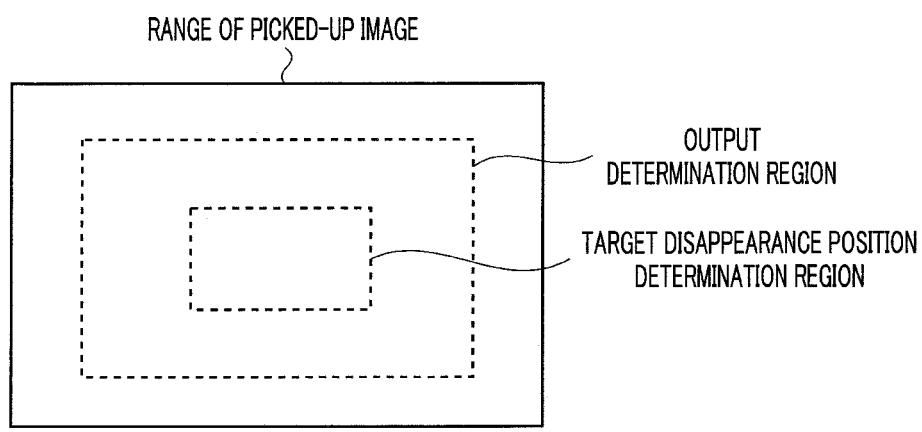
FIG. 15 is an explanatory diagram for explaining regions set in a picked-up image.

FIG. 15 is an explanatory diagram for explaining the above-described regions. As illustrated in FIG. 15, the target disappearance position determination region is set in a predetermined region at the substantially center of a region (range) of a picked-up image. In addition, the output determination region is set to the same region as the region of the picked-up image, or set, within the region of the picked-up image, so as to be larger than the target disappearance position determination region, for example. FIG. 15 illustrates an example in which the output determination region is set, within the region of the picked-up image, so as to be larger than the target disappearance position determination region.

When estimating the target position, the target position estimation section 19 reads out, from the end portion position storage section 15, the information on the position at the time of disappearance, and also the information on the target disappearance position determination region and the information on the output determination region. The target position estimation section 19 estimates the position of the image pickup target, determines whether or not the position at the time of the start of estimation, that is, the position at the time of disappearance is located in a region outside the target disappearance position determination region, and determines whether or not the estimated position is located in a region outside the output determination region.

When the position at the time of disappearance is a position within the target disappearance position determination region, the target position estimation section 19 does not output the position estimation result to the display control section 18. That is, if the estimation is started from the vicinity of the center of the image, the distance to be estimated becomes longer. Therefore, the target position estimation section 19 determines that the reliability of the position estimation of the image pickup target is extremely low and the position estimation is invalid, and does not cause the sign corresponding to the position estimation result to be displayed.

In addition, even in the case where the position estimation of the image pickup target is valid, the target position estimation section 19 outputs the position estimation result to the display control section 18, only when the estimated target position is located outside the output determination region.

That is, when the image pickup target is located within the output determination region, the operator can recognize the location of the image pickup target. Therefore, the target position estimation section 19 does not cause the sign corresponding to the position estimation result to be displayed. This can reduce an unnecessary sign and improve the visibility of the operator. Furthermore, in the case where the estimated target position is located in the vicinity of the center in the picked-up image, if the direction of the estimated target position with respect to the center of the picked-up image is illustrated as in FIG. 10, the direction may change largely due to an error of the estimation result, which results in a low reliability. For those reasons, it is preferable not to display the sign corresponding to the position estimation result, when the estimated target position is located within the output determination region. In this case, when the estimated target position is located outside the output determination region, the sign indicating the estimated position or direction of the image pickup target is displayed on the display screen 21a of the display apparatus 21.

The region in which the operator can recognize the location of the image pickup target is basically the same as the region of the picked-up image. Therefore, the output determination region may be set in the same region as the region of the picked-up image. However, due to the error of the estimated position of the image pickup target, even if the estimated position is located inside the region of the picked-up image, the actual target position might be located outside the region of the picked-up image. In such a case, there is a possibility that the estimation result is not displayed even if the image pickup target has disappeared. Therefore, in the present embodiment, the output determination region is set to be inside with respect to the region of the picked-up image depending on the accuracy of the estimated position. With such a configuration, when the image pickup target has disappeared, the estimation result can be surely displayed regardless of the error of the estimation result.

In addition, the example has been described in which both the determination based on the target disappearance position determination region and the determination based on the output determination region are performed. However, only one of the determinations may be performed.

Furthermore, the target position estimation section 19 may be configured not to output the position estimation result to the display control section 18 also when determining that the position at the time of disappearance is located within the region of the picked-up image. That is, also in this case, the target position estimation section 19 determines that the reliability of the position estimation of the image pickup target is low, and does not cause the sign corresponding to the position estimation result to be displayed.

It is preferable that the method for determining not to display the estimation result is set according to an allowable reliability of the position estimation of the image pickup target.

When not displaying the sign indicating the estimated position or direction of the image pickup target at the time of disappearance of the image pickup target, the display control section 18 may display, on the display screen 21a, a sign indicating that the image pickup target image cannot be detected in the picked-up image.

Thus, in the present embodiment, when the image pickup target image cannot be detected in the picked-up image, the sign indicating the estimated position of the image pickup target is not displayed, or displayed when the estimated position is located outside the range of the picked-up image. Such a configuration is capable of suppressing an erroneous operation by the operator due to the sign with relatively low reliability.

Note that description has been made on the example in which the image pickup target is a lumen such as an intestinal tract in each of the above-described embodiments. However, the image pickup target is not necessarily a lumen, but may be a diseased part such as a polyp. In addition, the embodiments may be applied not only to medical endoscopes but also to industrial endoscopes. Also in the case where the embodiments are applied to the industrial endoscopes, the image pickup target is not limited to a lumen, but may be various inspection objects such as parts to be inspected, or a path to reach the inspection objects.

Figure 16:
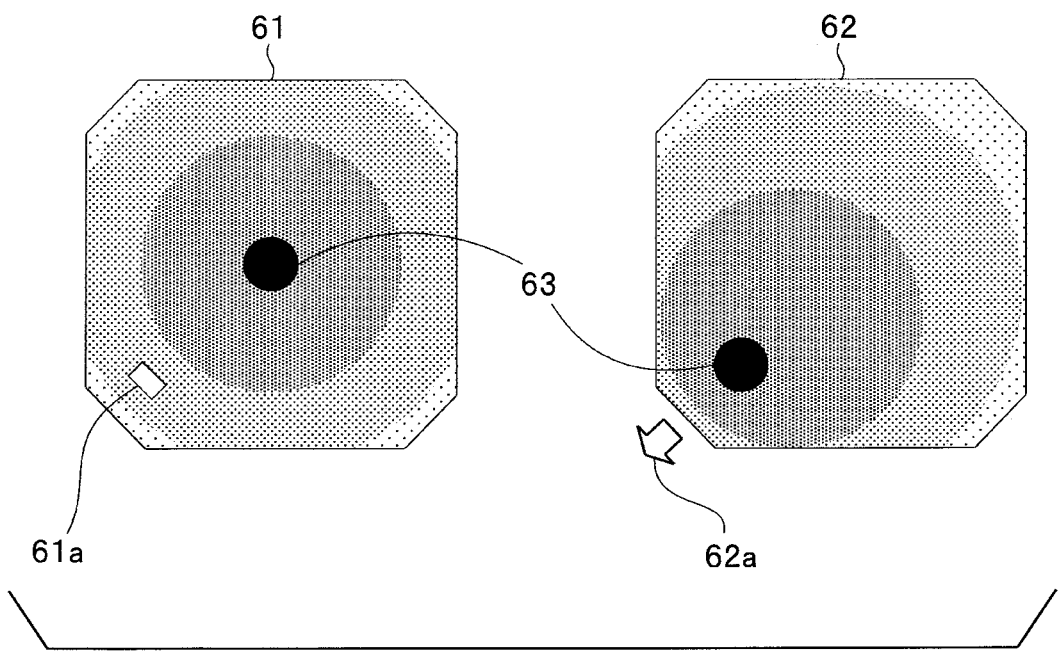
FIG. 16 is an explanatory diagram illustrating a display example in which an image pickup target image has disappeared in a case where an image pickup target is an inspection object.
Figure 17:
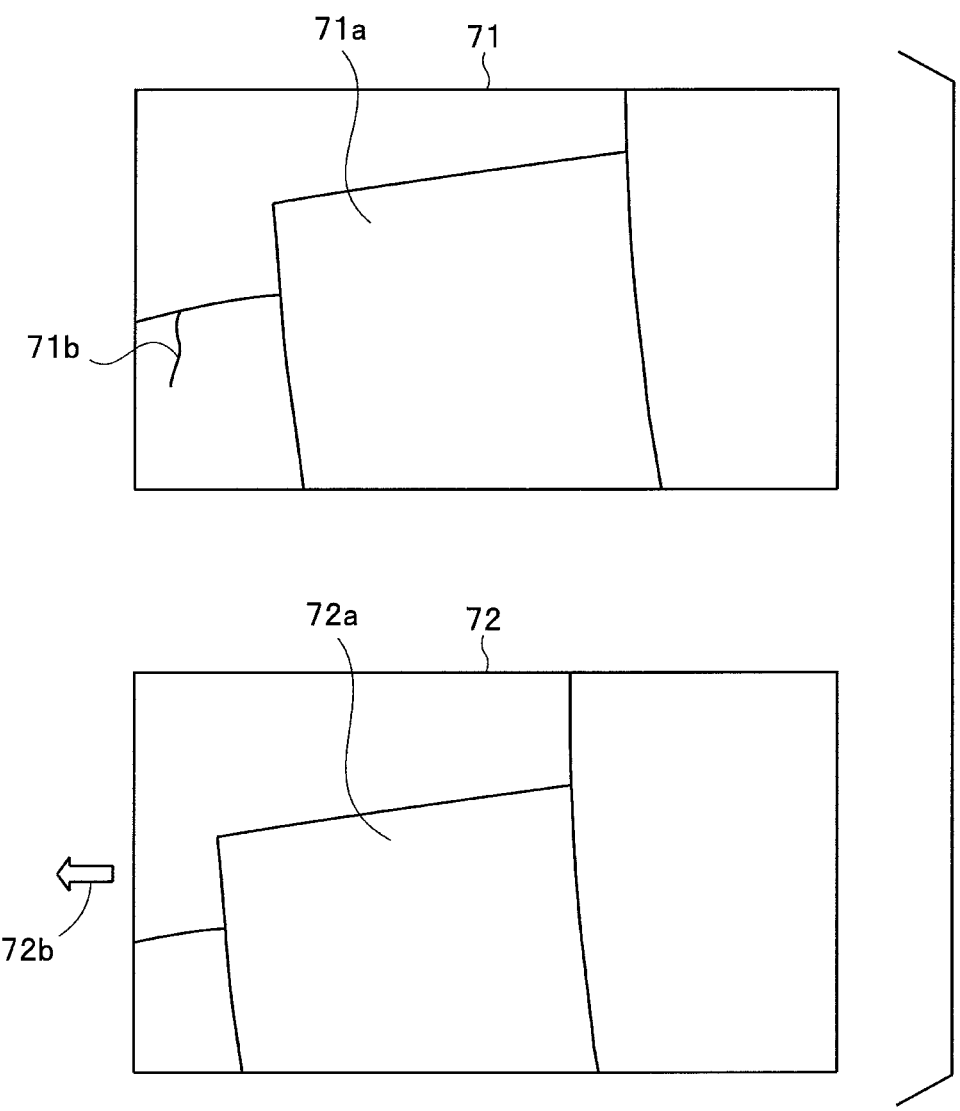
FIG. 17 is an explanatory diagram illustrating a display example in which the image pickup target image has disappeared in the case where the image pickup target is the inspection object.

FIGS. 16 and 17 are explanatory diagrams illustrating a display example in which the image pickup target image has disappeared in the case where the image pickup target is an inspection object. FIG. 16 illustrates an example of a picked-up image obtained by picking up an image inside of a pipe with an industrial endoscope, not illustrated. A picked-up image 61 of the inside of the pipe includes an image 63 of a lumen and an image 61a of the inspection object. In the example illustrated in FIG. 16, the image pickup target image is the image 61a of the inspection object. The picked-up image 62 in FIG. 16 illustrates an example in which the image 61a as the image pickup target image has disappeared from the picked-up image. However, even in this case, a sign 62a, which indicates that the estimated position of the inspection object as the image pickup target is located in the lower left direction relative to the picked-up image 62, is displayed. The sign 62a enables the worker to easily grasp in which direction the insertion portion should be directed in order to check the inspection object.

FIG. 17 illustrates an example of a picked-up image obtained by picking up an image of a turbine blade with an industrial endoscope, not illustrated. A picked-up image 71 includes an image 71a of the blade and an image 71b of a crack which is a defect part. In the example illustrated in FIG. 17, the image pickup target image is the image 71b of the crack. FIG. 17 illustrates an example in which an image 72a of the blade is included in a picked-up image 72, but the image 71b as the image pickup target image has disappeared from the picked-up image 72. However, even in such a case, a sign 72b, which indicates that the estimated position of the crack as the image pickup target is located in the left direction relative to the picked-up image 72, is displayed. The sign 72b enables the worker to easily grasp in which direction the insertion portion should be directed in order to check the crack.

Third Embodiment

Figure 18:
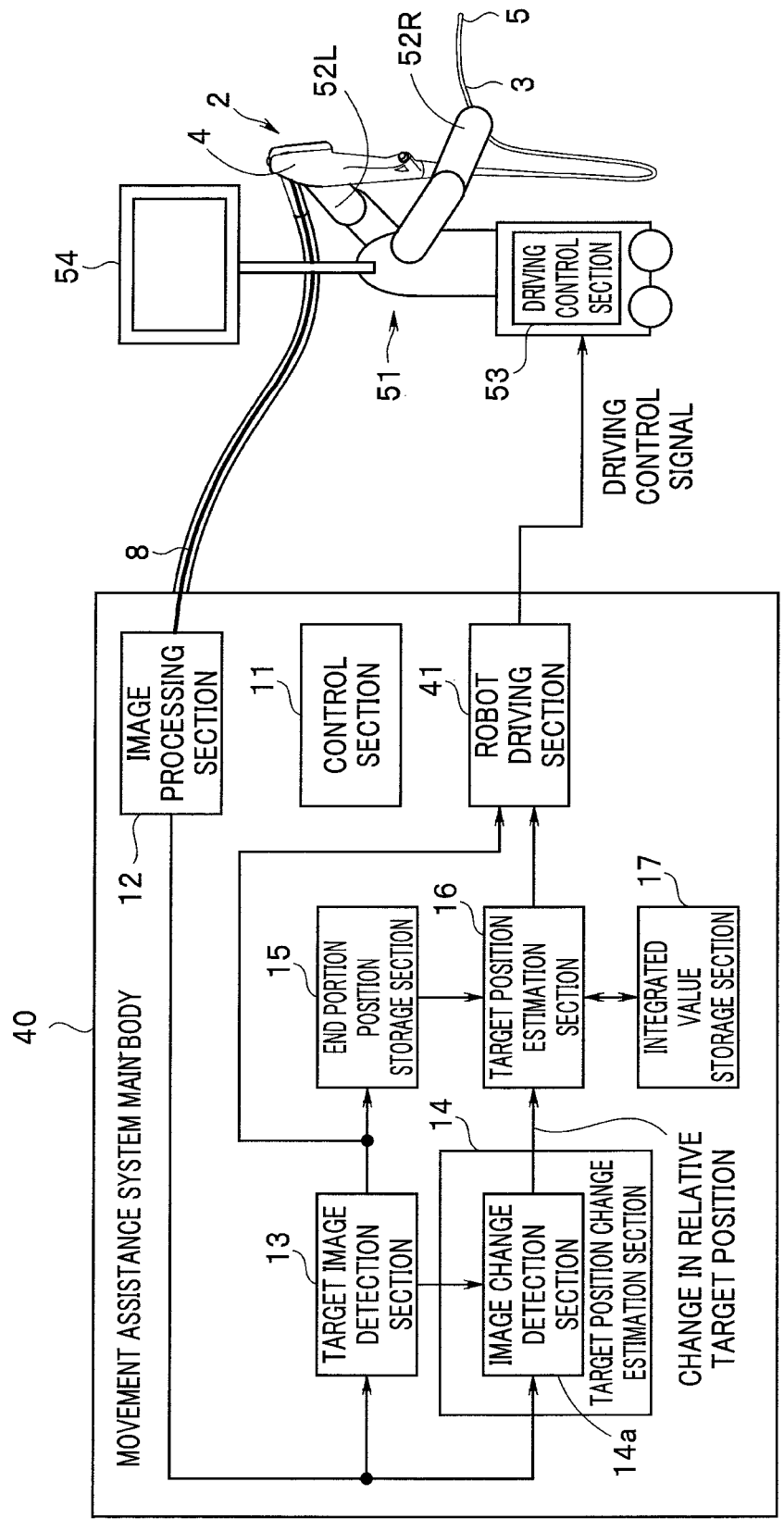
FIG. 18 is a block diagram illustrating a movement assistance system according to a third embodiment of the present invention.

FIG. 18 is a block diagram illustrating a movement assistance system according to the third embodiment of the present invention. Each of the above-described embodiments relates to a display to be performed based on the estimated position of the image pickup target. On the other hand, the present embodiment relates to a control of a movement of a mobile body, which includes an image pickup section and configured to move, based on the estimated position of the image pickup target. The third embodiment is applied to insertion control in a case where an insertion portion of an endoscope is inserted into a subject.

Also in the present embodiment, not only an insertion portion of a medical or industrial endoscope, but also a capsule endoscope, a catheter provided with an image pickup section, and the like are adoptable as a mobile body whose movement is controlled, for example. Furthermore, various kinds of known autonomously movable devices can be adopted as the mobile body.

As illustrated in FIG. 18, an insertion portion 3 of an endoscope 2 is inserted into a subject by an insertion robot 51. The insertion robot 51 includes arms 52L, 52R, and supports an operation portion 4 with the arm 52L and supports the insertion portion 3 with the arm 52R, for example. The arm 52R of the insertion robot 51 includes a delivering and retracting mechanism and a rotation mechanism, which are not illustrated, for the insertion portion 3, and the arm 52L includes a driving mechanism of a bending operation knob, not illustrated, disposed on the operation portion 4.

The insertion robot 51 includes a driving control section 53 configured to drive the arms 52L, 52R. The driving control section 53 of the insertion robot 51 drives the arms 52L, 52R according to a driving control signal from a movement assistance system main body 40. Note that the insertion robot 51 includes an operation panel 54, and a user performs operation for switching start and end of an automatic operation on an operation panel 54, for example. The operations to be performed automatically are not limited to all of the operations, but some of the operations may be performed automatically. For example, the operation of the bending operation knob may be performed automatically, and the insertion and extraction operation may be performed by the user on the operation panel 54.

An image pickup signals obtained by the image pickup section 7 (illustration is omitted) provided in the distal end rigid portion 5 of the insertion portion 3 of the endoscope 2 is supplied to an image processing section 12 of the movement assistance system main body 40 through a signal line 8.

The movement assistance system main body 40 in FIG. 18 is different from the movement assistance system main body 10 in FIG. 1 in that a robot driving section 41 is adopted in place of the display control section 18. The robot driving section 41 receives, from a target image detection section 13, information on a position on a picked-up image of the image pickup target image, and receives, from a target position estimation section 16, information on the estimated position of the image pickup target. The robot driving section 41 generates a driving control signal for driving each of the arms 52L, 52R of the insertion robot 51 such that the image pickup target image is included in the image pickup range, and outputs the generated driving control signal to a driving control section 53. That is, the robot driving section 41 performs driving control of the arms 52L, 52R such that the image pickup target image is picked up. When the image pickup target image has disappeared from the picked-up image, based on the position estimation result of the image pickup target received from the target position estimation section 16, the robot driving section 41 performs the driving control such that the image pickup target image is picked up by driving the arms 52L, 52R. Such driving control enables smooth insertion of the insertion portion 3 into the intestinal tract, and the like.

Thus, the present embodiment enables the control of the insertion of the insertion portion based on the image pickup target image in the picked-up image. In addition, in the present embodiment, when the image pickup target image has disappeared from the picked-up image, the position of the image pickup target relative to the picked-up image is estimated, to control the insertion of the insertion portion based on the estimation result. Therefore, the present embodiment is capable of performing effective insertion assistance for surely guiding the insertion portion in the deep part direction of the lumen, or the like.

Note that the control section 11, the image processing section 12, the target image detection section 13, the target position change estimation section 14, the target position estimation sections 16, 19, the display control section 18, etc., in the above-described embodiments may be configured by combining dedicated circuits and a plurality of general-purpose circuits, and as necessary, configured by combining a processor such as a microprocessor, a CPU, and the like that operate according to the software programmed in advance, or a sequencer. In addition, a design is possible in which a part of or all of the controls of any of the above-described sections are executed by an external apparatus. In such a case, a wired or a wireless communication circuit is disposed between the sections and the external apparatus. An embodiment may be possible in which characteristic processing or additional processing in each of the embodiments is performed by an external apparatus such as a server or a personal computer. That is, the present application covers a case where the feature of the present invention is achieved by a plurality of apparatuses in cooperation with each other. For the communication in such a case, Bluetooth (registered trademark), Wi-Fi (registered trademark), telecommunication lines, and the like are used. In addition, the communication in such a case may be performed by using an USB, and the like. The dedicated circuit, the general-purpose circuits, and a control section may be integrated and configured as an ASIC (application-specific integrated circuit).

Among the above-described techniques, the control and functions mainly described in the flowchart can be set by a program, and the above-described control and functions can be implemented by the program being read and executed by a computer. The entirety or a part of the program can be recorded or stored as a computer program product in a portable medium such as a flexible disk, CD-ROM, a non-volatile memory, or the like, or a storage medium such as hard disk, a volatile memory, or the like. The program can be distributed or provided at the time of product shipment or through a portable medium or a communication line. It is possible for a user to easily implement the movement assistance system according to the present embodiment by downloading the program through a communication network to install the program into a computer, or installing the program from a recording medium into the computer.

The present invention is not limited to the above-described embodiments, and it goes without saying to embody the invention by modifying the constituent elements in a range without departing from the gist of the invention at the practical stage. In addition, various inventions can be achieved by appropriately combining the plurality of constituent elements disclosed in each of the above-described embodiments. Some of the constituent elements may be deleted from all the constituent elements shown in the embodiments, for example. Furthermore, constituent elements over different embodiments may be appropriately combined.

What is claimed is:

1. A movement assistance system comprising:
a memory; and
a processor configured to:

receive picked-up images acquired by an image pickup apparatus fixed to a mobile body, detect an image of an image pickup target included in each of the picked-up images, and detect a position in each of the picked-up images of the detected image of the image pickup target;

cause the memory to store the position in each of the picked-up images of the detected image of the image pickup target;

estimate a change in the position of the image pickup target relative to each of the picked-up images, by detecting a change in the received picked-up images;

estimate the position of the image pickup target relative to each of the picked-up images based on information on the position stored in the memory and an estimation result of the change in the position of the image pickup target, to output a position estimation result, and perform control for causing a display apparatus to display the position estimation result, when detecting a disappearance state in which the image of the image pickup target is not detected on the picked-up images;

perform control not to output the position estimation result, in a case where the image of the image pickup target is not detected, when the position stored in the memory immediately before the image of the image target is brought into the disappearance state indicates a position inside a target disappearance position determination region as a predetermined region in each of the picked-up images; and perform control for causing the display apparatus not to display the position estimation result, when detecting, after the image of the image pickup target is brought into the disappearance state, that a position indicated by the position estimation result is a position inside an output determination region as a region for determining whether or not to output the position estimation result, wherein the output determination region is a region inside with respect to a range of each of the pick-up images and the target disappearance position determination region is a region inside with respect to the output determination region.

2. The movement assistance system according to claim 1, wherein when detecting the disappearance state, the processor is configured to:

start estimating the change in the position of the image pickup target relative to the each of the picked-up images; and estimate the position of the image pickup target relative to each of the picked-up images, based on information on the position stored in the memory immediately before a start of the disappearance state and the estimation result of the change in the position of the image pickup target.

3. The movement assistance system according to claim 1, wherein the mobile body comprises an insertion portion of an endoscope, and wherein the image pickup apparatus is disposed in a distal end portion of the insertion portion of the endoscope.

4. The movement assistance system according to claim 1, wherein the processor is configured to estimate the change in the position of the image pickup target by an optical flow estimation using the picked-up images.

5. The movement assistance system according to claim 4, wherein the processor is configured to detect, on the picked-up images sequentially received by the processor, a moving amount and a moving direction of a predetermined tracking point in the picked-up images, and outputs a detection result as the estimation result of the change in the position of the image pickup target.

6. The movement assistance system according to claim 4, wherein, when, on the picked-up images sequentially received by the processor, moving trajectories of a plurality of tracking points set in each of the picked-up images respectively form circular-arc shapes having a common rotation center, the processor is configured to determine that the position of the image pickup target changes in a rotation direction around the rotation center, to obtain the estimation result.

7. The movement assistance system according to claim 4, wherein when, on the picked-up images sequentially received by the processor, moving trajectories of a plurality of tracking points set in each of the picked-up images respectively form linear lines extending radially from a common point, the processor is configured to determine that the position of the image pickup target changes in an optical axis direction of the image pickup apparatus, to obtain the estimation result.

8. The movement assistance system according to claim 1, wherein the processor is configured to estimate the change in the position of the image pickup target by machine learning using the picked-up images.

9. The movement assistance system according to claim 1, wherein the processor is configured to cause the display apparatus to display each of the picked-up images and a direction of the image pickup target relative to each of the picked-up images, based on the picked-up images and the position estimation result.

10. The movement assistance system according to claim 1, wherein the processor is configured to cause the display apparatus to display each of the picked-up images and the position of the image pickup target relative to each of the picked-up images, based on the picked-up images and the position estimation result.

11. The movement assistance system according to claim 1, wherein, when detecting that the disappearance state in which the image of the image pickup target is not detected on the picked-up images continues for a time period longer than a predetermined elapsed time, or a distance from each of the picked-up images to the estimated image pickup target is longer than a predetermined direct distance or a predetermined route length, the processor is configured to cause the display apparatus not to display the position estimation result and/or causes the display apparatus to display a sign indicating that a reliability of the position estimation result decreases.

12. The movement assistance system according to claim 1, further comprising:

a driving control circuit configured to cause the mobile body to displace in a direction of an optical axis of the image pickup apparatus, a direction orthogonal to the direction of the optical axis, and in a rotation direction around the optical axis; and a driving circuit configured to receive the position estimation result from the processor to generate a control signal for controlling the driving control circuit.

13. A movement assistance method comprising:

receiving picked-up images acquired by an image pickup apparatus fixed to a mobile body, detecting an image of an image pickup target included in each of the picked-up images, and detecting a position in each of the picked-up images of the detected image of the image pickup target;

causing a memory to store the position in each of the picked-up images of the detected image of the image pickup target;

estimating a change in the position of the image pickup target relative to each of the picked-up images, by detecting a change in the picked-up images;

estimating the position of the image pickup target relative to each of the picked-up images based on information on the position stored in the memory and an estimation result of the change in the position of the image pickup target, to output a position estimation result, and performing control for causing a display apparatus to display the position estimation result, when detecting a disappearance state in which the image of the image pickup target is not detected on the picked-up images;

performing control not to output the position estimation result, in a case where the image of the image pickup target is not detected, when the position stored in the memory immediately before the image of the image target is brought into the disappearance state indicates a position inside a target disappearance position determination region as a predetermined region in each of the picked-up images; and performing control for causing the display apparatus not to display the position estimation result, when detecting, after the image of the image pickup target is brought into the disappearance state, that a position indicated by the position estimation result is a position inside an output determination region as a region for determining whether or not to output the position estimation result, wherein the output determination region is a region inside with respect to a range of each of the pick-up images and the target disappearance position determination region is a region inside with respect to the output determination region.

* * * * *